(12) United States Patent
Blumenthal et al.

(10) Patent No.: US 6,649,352 B1
(45) Date of Patent: Nov. 18, 2003

(54) METHOD OF EVALUATING MYELOSUPPRESSIVE STATE

(75) Inventors: Rosalyn D. Blumenthal, Belleville, NJ (US); Walter Lew, Caldwell, NJ (US); Malik Juweid, Bloomfield, NJ (US); Rita Alisauskas, Hopatcong, NJ (US); Zhiliang Ying, East Brunswick, NJ (US); David M. Goldenberg, Mendham, NJ (US)

(73) Assignee: Center for Molecular Medicine and Immunology, Belleville, NJ (US)

( * ) Notice: Subject to any disclaimer, the term of this patent is extended or adjusted under 35 U.S.C. 154(b) by 0 days.

(21) Appl. No.: 09/482,730

(22) Filed: Jan. 14, 2000

Related U.S. Application Data

(60) Provisional application No. 60/118,071, filed on Jan. 29, 1999.

(51) Int. Cl.$^7$ .................. G01N 33/53; G01N 33/567; C07K 16/24
(52) U.S. Cl. .......... 435/7.1; 435/7.2; 435/7.21; 530/351; 530/387.9; 530/388.23
(58) Field of Search ................. 530/350, 351, 530/399, 387.9, 388.23; 435/7.1, 7.2, 7.21

(56) References Cited

U.S. PATENT DOCUMENTS

| | | | |
|---|---|---|---|
| 5,223,395 A | | 6/1993 | Gero |
| 5,360,716 A | | 11/1994 | Ohmoto et al. |
| 5,554,512 A | * | 9/1996 | Lyman et al. ............ 435/69.5 |
| 5,772,998 A | | 6/1998 | Dasch et al. |

FOREIGN PATENT DOCUMENTS

| | | |
|---|---|---|
| EP | 288088 A2 | 4/1988 |
| WO | WO93/06489 A1 | 4/1993 |
| WO | WO94/26891 A2 | 11/1994 |
| WO | WO96/400098 A2 | 12/1996 |
| WO | WO97/06251 A1 | 2/1997 |

OTHER PUBLICATIONS

Stratagene catalogue 1988. p. 39.*
Scadden DT et al. AIDS 1994, vol 8, pp. 193–196. In vitro effects of stem–cell factor or interleukin–3 on myelosuppression associated with AIDS.*
Blumenthal RD et al. Exp Hematol. 1998, vol. 26; pp. 859–868. Myelosuppressive changes from single or repeated doses of radioantibody therapy: effect of bone marrow transplantation, cytokines, and hematopoietic suppression.*
Strait RT, Ruddy RM, Friedland LR, Duncan KM, Wilmott RW. 1997, Acad Emerg Med vol. 4, pp. 44–51. A pilot study of the predictive value of plasma TNF–alpha and interleukin 1 beta for *strptococcus pneumoniae* bacterimia in febrile children.*
XP–000920913 Blumenthal R.D.: "Plasma FLT3–L levels predict bone marrow recovery from myelosuppressive therapy".
03013864 Patent Abstracts of Japan vol. 0151, No. 31.

* cited by examiner

Primary Examiner—Prema Mertz
(74) Attorney, Agent, or Firm—Foley & Lardner

(57) ABSTRACT

The invention provides kits and methods for evaluating the myelosuppressive state of a patient. These methods and kits provide a useful adjunct for cytotoxic and myelosuppressive therapies. By establishing threshold levels of certain cytokines as a surrogate for myelosuppression, treatment protocols can be optimized to reduce myelotoxicity, while maximizing effective dose.

6 Claims, 3 Drawing Sheets

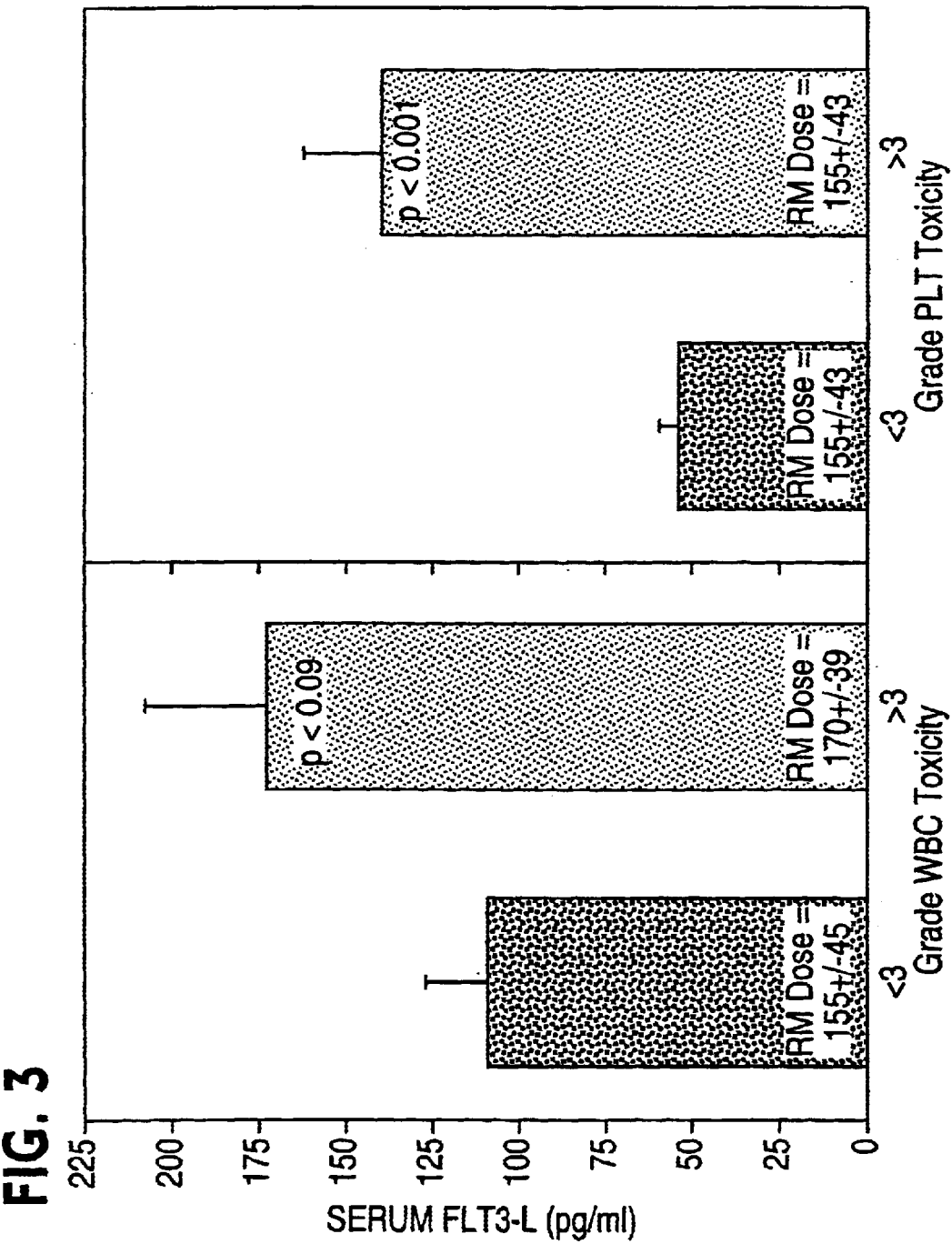

METHOD OF EVALUATING MYELOSUPPRESSIVE STATE

This application claims the benefit of Provisional Application No. 60/118,021 filed Jan. 29, 1999.

This work was supported in part by United States Public Health Service grant RO1 CA49995 (RDB) and R23 CA39841 (DMG) from the National Institutes of Health.

GOVERNMENT LICENSE RIGHTS

The U.S. Government has a paid-up license in this invention and the right in limited circumstances to require the patent owner to license others on reasonable terms as provided for by the terms of grant numbers CA 49995 06 and CA 39841, awarded by the National Institutes of Health.

BACKGROUND OF THE INVENTION

Both chemotherapy and radioimmunotherapy induce dose-limiting myelosuppression. In fact, chemotherapy-induced myelosuppression is the most common dose-limiting, and potentially fatal, complication of cancer treatment. Maxwell et al., Semin. Oncol. Nurs. 8:113–123 (1992); Blijham, Anticancer Drugs 4:527–533 (1993). Drug-induced hematopoietic toxicity is a common reason for curtailing high dose chemotherapy in cancer patients (Boesen et al., Biotherapy 6:291–302 (1993)), and higher dose chemotherapy is only possible in conjunction with bone marrow transplantation (BMT), autologous stem cell infusion, and treatment with hematopoietic growth factors.

During the recovery period after anticancer myelosuppressive therapy, hematopoietic progenitor cells become mitotically active in order to replenish the marrow compartment and remain hyperproliferative even after normalization of peripheral white blood cells (pWBCs) and platelets (PLTs). At this stage, the progenitors are more radio- and chemo-sensitive. Dosing patients with additional cytotoxic therapy during this phase will likely result in more severe toxicity.

As a general model of myelosuppressive therapy, acute damage and recovery of hematopoietic stem and precursor cells following whole-body irradiation also has been studied extensively. Testa et al., Anticancer Res. 5:101–110 (1985); Sado et al., Int. J. Radiat Biol 53:177–187 (1988); Meijne et al., Exp. Hematol. 19:617–623 (1991). External beam irradiation results in long-term damage of hematopoietic stem cells, which manifests with the presence, but at sub-optimal levels, of mitotically active, hematopoietic progenitor cells (CFU-S) 3–6 months after treatment. Lorimore et al., Int. J. Radiat Biol 57:385–393 (1990); Lord et al., Int. J. Radat. Biol. 59:211–218 (1991). Persistent depletion of femoral and splenic CFU-S (colony forming unit-spleen), CFU-GM (colony forming unit-granulocytic-monocytic) and BFU-E (burst forming unit-erythroid) can occur, even though the peripheral blood contains normal cell numbers. Grande et al., Int. J. Radiat. Biol. 59:59–67 (1993). Severe reduction in the supportive stroma has also been reported. Tavassoli et al., Exp. Hematol. 10:435–443 (1992). Following radiation exposure, recovery proceeds by repair of sublethal cellular injury and compensatory cellular repopulation by the surviving fraction. Hall in *Radiobiogy for the Radiobiologist* (Harper & Row 1978); Jones et al., Radiation Res. 128:256–266 (1991).

Normal white blood cell (WBC; >4000/mm$^3$) and platelet (PLT; >100,000/mm$^3$) counts are the usual markers for patient tolerance to repetitive myelosuppressive treatment. However, preclinical and clinical evidence suggests that peripheral counts are not a reliable surrogate for predicting complete myelosuppressive recovery. Although WBC and PLT counts may appear normal, the primitive stem and progenitor cell compartments are not fully recovered from previous myelosuppressive therapy.

Further cytotoxic treatment while stem cells and progenitor cells are rapidly proliferating can result in more severe myelotoxicity or even death. One solution to this problem is to collect bone marrow (BM) aspirates and use a long-term culture system to quantitate high proliferative potential CFC (HPP-CFC) or long term culture initiating cells (LTC-IC). Eaves et al., Tiss. Culture Meth. 13:55–62 (1991); McNiece et al., Blood 75:609–612 (1989). While this method can provide the needed information, such assays take 3–6 weeks to perform, and thus are not clinically useful.

During hematopoiesis, pluripotent stem cells differentiate and proliferate in multiple lineages. The process proceeds under the permissive influence of "early" and "late" hematopoietic cytokines. Lowry et al., J. Cell Biochem. 58:410–415 (1995). "Early" stimulatory factors include SCF, FLT-3-L, IL-1, IL-3, IL-6, and IL-11. In addition to these positive regulators, hematopoiesis is also controlled by inhibitory cytokines. Negative regulation of myelopoiesis occurs through several inhibitory cytokines, most notably MIP-1α (Cooper et al., Expt. Hematol. 22:186–193 (1994); Dunlop et al., Blood 79:2221–2225 (1992)), TGFβ3 (Jacobsen et al., Blood 78:2239–2247 (1991); Maze et al., J. Immunol. 149:1004–1009 (1992)) and TNFα (Mayani et al., Eur. J. Haematol. 49:225–233 (1992)).

Thus far a temporal change in these inhibitory peptides as a function of time after cytotoxic therapy has not been quantitated. It is known, however, that under stressful conditions, such as irradiation, chemotherapy, blood loss, infection or inflammation, both stimulatory and inhibitory growth factors play a major role in cellular adaptation processes. Cannistra et al., Semin. Hematol. 25:173–188 (1988). Under stress, the quiescent CFU-S component of the stem cell compartment is triggered into active cell cycling and returns to the predominantly $G_0 G_1$ phase once normal bone marrow cellularity is restored. Becker et al., Blood 26:296–304 (1965).

The recent literature has highlighted several important areas where a noninvasive method to monitor myelorecovery could have considerable clinical benefit. For example, to improve the safety and cost effectiveness of high-dose regimens, hematopoietic cell support (cytokines) has been used to accelerate marrow recovery following myeloablative therapy. This approach results in an earlier recovery of peripheral blood counts, but the proliferative status of the marrow remains unknown and could be in a very active and sensitive state.

Another relevant example pertains to the use of allogeneic or autologous BMT, or more recently peripheral stem cell transplantation (SCT) following myelosuppressive or myeloablative therapy. Under those conditions, hematopoiesis is characterized by a prolonged and severe deficiency of marrow progenitors for several years, especially of the erythroid and megakaryocyte types, while the peripheral WBCs and PLTs have reached relatively normal values within a few weeks. Therefore, successful engraftment can not be measured by normalization of WBCs or PLTs, but requires another type of marker, perhaps one associated with normal marrow stromal function. Domensch et al., Blood 85:3320–3327 (1995). More information is needed to determine 'true' myelorecovery when either BMT or SCT is utilized. Talmadge et al., Bone Marrow Transplant. 19(2):161–172 (1997).

Yet, another area where a noninvasive measure of myelorecovery may be useful is for scheduling leukapheresis. Since patient-to-patient variability in time to marrow recovery is quite variable following G-CSF stem cell mobilization, it is difficult to predict the best time for this procedure. Identification of one or more markers of myelotoxic nadir and recovery could advance SCT technology. Shpall et al., Cancer Treat. Res. 77:143–157 (1997).

One investigator has shown that after allogeneic or autologous BMT, a rise in endogenous G-CSF levels precedes and correlates with myeloid engraftment. Cairo et al., Blood 79(7):1869–1873 (1992). Moreover, in patients suffering from acute bacterial infections, whose rate of myelopoiesis must adapt to the enhanced demand, G-CSF, but not GM-CSF, was elevated. Selig et al., Blood 79:1869–1873 (1995). Additional studies demonstrated that the stem cell subset responsible for reconstitution is responsive to GM-CSF, IL-3, IL-6, and SCF. Wagemaker et al., Stem Cells 13:165–171 (1995). Other reports have quantified one or more cytokines during a myelosuppressive episode. Sallerfors et al., Br. J. Hematol. 78:343–351 (1991); Baiocchi et al., Cancer Research 51:1 297–1303 (1996); Chen et al., Jap. J. Clin. Oncol. 26:18–23 (1996). Heretofore, however, no one looked at the recovery phase following myelosuppression, and there exists no correlation with the ability to redose without severe toxicity. A relatively new stromal cell-produced positive stimulatory cytokine, FLT-3-L (Brasel et al., Blood 88:2004–2012 (1996); Lisovsky et al., Blood 88(10):3987–97 (1996)), has not been studied at all to date regarding either constitutive or induced hematopoiesis.

Therefore, a need exists in the art for improved methods, and kits for implementing them, for predicting myelosuppressive recovery in conjunction with the foregoing deficient therapeutic techniques. Such methods could be used to help optimize treatment, informing the clinician of the appropriate timing of treatment, thus avoiding toxic effects, while maximizing efficacious ones. Provided such a method, the art would posses new, optimized methods of treatment.

SUMMARY OF THE INVENTION

It is therefore an object of the invention to provide kits and methods for evaluating the myelosuppressive state of a patient. According to this object, the invention provides a kit which contains at least one cytokine-specific detection reagent that is adapted to detect a threshold level of a cytokine, which correlates with the myelosuppressive state. In one embodiment, the cytokine specific reagent is specific for FLT3-L, TNF-α or TGF-β, and the reagent may comprise an antibody or antibody fragment.

Also according to this object of the invention, a method of assessing the myelosuppressive state of a patient is provided. This method entails comparing the amount of at least one cytokine in a patient sample with a threshold level, thereby gauging the myelosuppressive state of the patient. In one embodiment, the cytokine specific reagent is specific for FLT3-L, TNF-α or TGF-β, and the reagent may comprise an antibody or antibody fragment.

It is another object of the invention to provide an improved method of treating cancer. Further to this object, a method is provided where a patient is administered an effective amount of an anti-cancer agent and the level of at least one cytokine is compared with a threshold level. In one embodiment, the cytokine is FLT3-L, TNF-α or TGF-β. In other aspects, the method involves using the threshold level to guide treatment, so that when the threshold is approached or crossed, treatment is halted or decreased until the threshold is no longer approached or crossed.

BRIEF DESCRIPTION OF THE DRAWINGS

FIG. 3. Plasma FLT3-L levels (mean±SEM) for patients sorted by grade toxicity—those<grade 3 (27–28 patients) and those>grade 3 toxicity (11–12 patients). Average RM dose for all groups is noted in the base of the vertical bars and significance (t-test) noted at the top of the bar.

DETAILED DESCRIPTION OF THE INVENTION

A. Definitions

Figure 1:
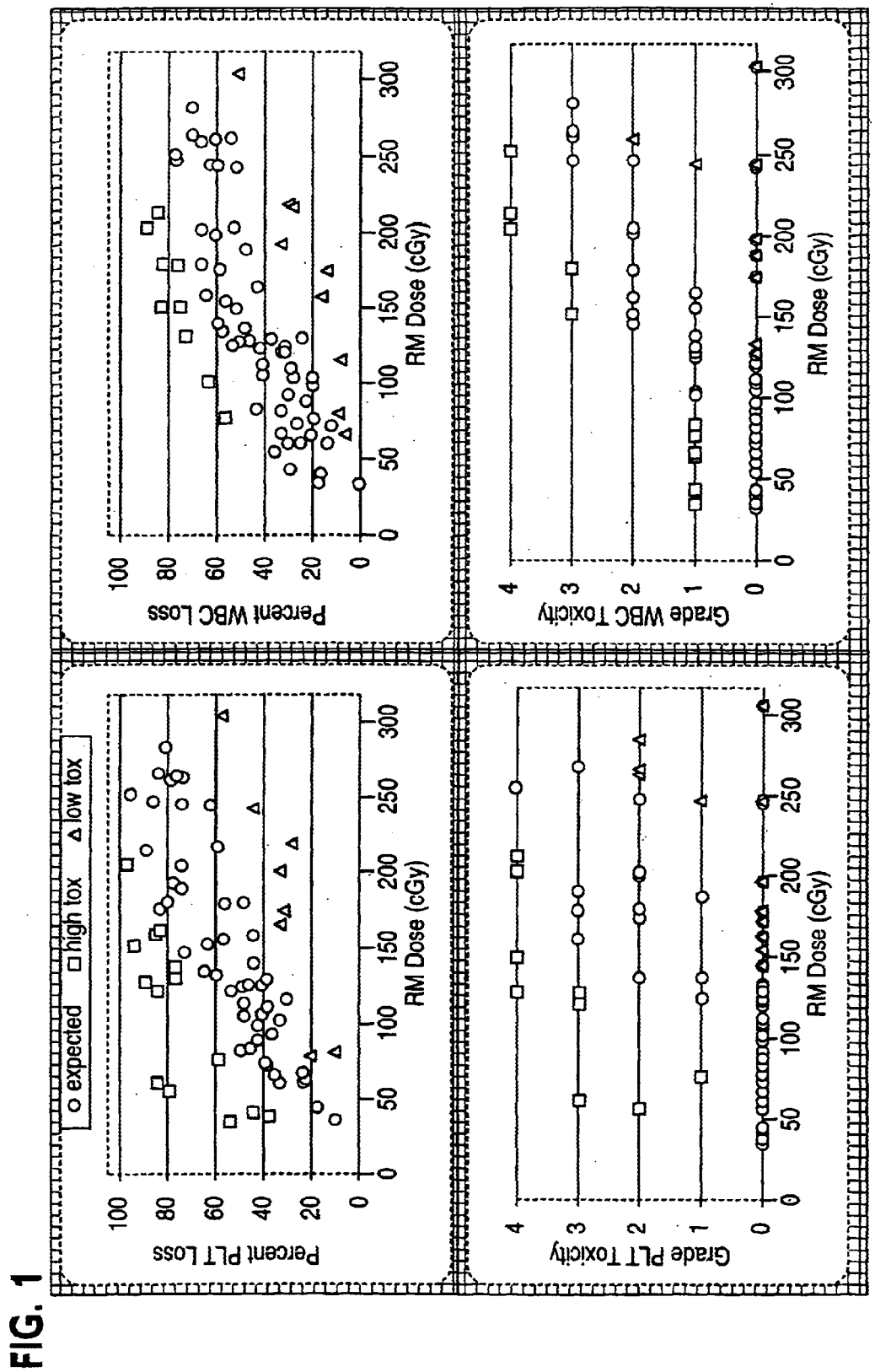
FIG. 1. Scattergram representation of 76 patients given different red marrow doses of RAIT and the (a) percent PLT loss; (b) percent WBC loss, (c) grade PLT toxicity and (d) grade WBC toxicity shown. All patients had normal initial pWBC and gels PLT counts at the time of cytotoxic therapy (RAIT). {Open circles=normal toxicity; closed squares= higher than expected toxicity and open triangles=lower than expected toxicity}. Twenty-three patients were omitted because they either had BM involvement on two or more known metastases or they had higher than normal values of either pWBCs ($>10,000/mm^3$) or PLTs ($>5 \times 10^5/mm^3$).

As used herein, "myelosuppression" refers to the suppression of one or more components of hematopoiesis, which manifests in aberrant levels of one or more of the cell types that are the products of this process. For a review of hematopoiesis, and characteristics of hematopoietic cells, see *Clinical Immunology: Principles and Practice*, Vol. 1, Ch. 2, pp. 15–24 (Lewis and Harriman, eds. Mosby—Year Book, Inc. 1996), which pages are hereby incorporated by reference. On a general level it refers to decreases in white blood cell and/or platelet counts. It also refers, on a more specific level, to suppression, relative to normal levels, of one or more of the following cells that result from hematopoiesis: B-cells, T-cells, natural killer cells, dendritic cells, macrophages, neutrophils, eosinophils, basophils, mast cells and platelets. On the other hand, therefore, "myelorecovery" is the opposite of myelosuppression.

As used herein, a "stimulatory cytokine" is one that promotes hematopoiesis at one or more stages of differentiation. Stimulatory cytokines include SCF, FLT-3-L, IL-1, IL-3, IL-6, IL-11, and others known to the skilled artisan. Obviously, certain interleukins, historically referred to as "lymphokines" also are included in this term.

As used herein an "inhibitory cytokine" has a negative effect on one or more stages of hematopoiesis. Exemplary inhibitory cytokines include MIP-1α, TGFβ3, TNFα and others known in the art.

As used in a general sense herein, unless otherwise indicated by context, the term "antibody" includes "antibody fragment".

B. Principles of the Invention

The invention relates to the ability to predict myelorecovery by monitoring various inhibitory and stimulatory cytokines. The present inventors have discovered that threshold levels of certain cytokines can be used to guide the health care professional in using myelosuppressive therapies. In particular, these threshold levels provide a marker, indicating whether or not a patient will tolerate such therapy. A common application is in monitoring cytoreductive therapies, where the subject threshold levels are used to decide whether a patient is sufficiently recovered from one dose of a myelosuppressive agent to tolerate another, perhaps increased dose.

The cytokine levels monitored in the inventive methods include the so-called "early" stimulatory cytokines and the inhibitory cytokines. To be useful in these methods and kits, a statistically significant threshold level of the cytokine (or a combination of them) that correlates with myelosuppressive recovery should be ascertainable. The artisan will be familiar with such statistical analysis and may readily ascertain such threshold levels, as demonstrated below in the Examples.

In a broad sense, a threshold level may be a level that is found in a normal volunteer, with any deviation associated with myelosuppression being indicative of that state. In particular, the threshold level should be set such that "specificity" [(true negative) divided by (true negative plus total population)], "accuracy" [(true positive plus true negative) divided by (total population)] and "sensitivity" [(true positive) divided by (true positive plus false negative)] are maximized. The artisan will recognize, however that such maximization often represents a trade-off, since higher specificity, accuracy or sensitivity can result in the others being lowered. Some inventive methods yield greater: than about 65% specificity, accuracy and sensitivity, while some preferred methods yield at least about 75% specificity, accuracy and sensitivity.

"Early" stimulatory cytokines include, but are not limited to, SCF, FLT-3-L, IL-1, IL-3, IL-6, and IL-11. These factors are thought to be involved in the early stages of myelorecovery. Thus, when they are present, the damage should be at its worst, whereas, when their levels are decreasing, a certain amount of recovery has already taken place. Accordingly, a statistically significant threshold should be ascertainable, which, when exceeded, counsels against continued therapy or indicates reducing the dose. On the other hand, as a patient progresses beyond these early stages of recovery, levels will drop and treatment may resume or dose may be increased.

Inhibitory cytokines, in contrast, likely are present when myelosuppressive recovery is virtually complete, when the process is turning itself off. Hence, the threshold level for these cytokines will represent a minimum level, below which therapy should be reduced or halted. Exemplary inhibitory cytokines include MIP-1α, TGFβ3 and TNFα.

The invention also contemplates the usefulness of trends in predicting myelorecovery. Thus, it is possible that the absolute amount of plasma cytokine needs to be coupled with the duration or time since the cytokine reached its peak. For example, as seen below in the working examples, since the values for FLT3-L ranged from below 100 pg/ml to over 400 pg/ml, it is possible that readings of FLT3-L within or just above the normal range may need to be evaluated again a few days later to determine whether plasma FLT3-L is on the rise, or is returning back down to baseline levels after being elevated. It is contemplated that those patients whose FLT3-L levels have returned to normal and have maintained a normal baseline level for several weeks can tolerate higher doses than patients who have recovered only days earlier from a myelosuppressive episode and elevated FLT3-L. This provides an explanation of the low toxicity group that does not strictly correlate with any of the cytokines measured.

C. Kits of the Invention

The kits according to the invention typically comprise at least one cytokine-specific detection reagent. Some kits contain at least two cytokine-specific detection reagents. In most cases, each reagent will be adapted to detect a threshold level of cytokine, which correlates with the myelosuppressive state of a patient. In one aspect, the invention contemplates a kit for assessing the myelosuppressive state of a patient, which is useful in guiding the physician in choosing an optimal treatment regimen. They may be applied, for example, to monitor myelosuppressive treatments, to monitor efficacy of myelostimulatory treatments and to monitor recovery from myelosuppressive disorders.

Some embodiments of the present kits contain the detection reagent in association with a suitable testing substrate. Suitable substrates include "dipsticks," test-strips, microtiter plates, microscope slides, and the like. The kits of the invention generally implement the methods, described below, and should be read in that context.

1. Cytokine-specific Detection Reagents

The cytokine-specific detection reagent of the kit generally confers the ability to detect specifically the cytokine of interest, like those mentioned above, in some cases quantitatively. Typically this reagent will be able to bind specifically to a cytokine, and will be detectable, directly or indirectly. For instance, the reagent may be an antibody, and may comprise a detectable label, such as a radionuclide, an enzyme or a 30 fluorescent tag. The label may be detected, for example, using conventional immunoassays, which include enzyme-linked immunosorbant assays (ELISAs), radioimmunoassays (RIAs), and the like. Suitable methods can be found in *Current Protocols in Molecular Biology*, Chapter 11 (Ausubel et al., eds., John Wiley & Sons, Inc. 1997), which is hereby incorporated by reference.

Due to their recognized ability to bind specifically and to their ease of production, antibodies are contemplated as a means of conferring the cytokine-binding ability of the detection reagent. Antibodies include, but are not limited to polyclonal antibodies, monoclonal antibodies (mAbs), humanized or chimeric antibodies, single chain antibodies including single chain Fv (scFv) fragments, Fab fragments, F(ab')$_2$ fragments, fragments produced by a Fab expression library, epitope-binding fragments, and multivalent forms of any of the above.

In general, techniques for preparing polyclonal and monoclonal antibodies as well as hybridomas capable of producing the desired antibody are well known in the art (Campbell, *Monoclonal Antibody Technology: Laboratory Techniques in Biochemisty and Molecular Biology*, (Elsevier Science Publishers 1984); St. Groth et al., J. Immunol. Methods 35:1–21 (1980); Kohler and Milstein, Nature 256:495–497 (1975)), the trioma technique, the human B-cell hybridoma technique (Kozbor et al., Immunology Today 4:72 (1983); Cole et al., in *Monoclonal Antibodies and Cancer Therapy*, Alan R. Liss, Inc. (1985), pp. 77–96). Affinity of the antisera for the antigen may be determined by preparing competitive binding curves, as described, for example, by Fisher, Chap. 42 in: *Manaual of Clinical Immunology*, 2d ed., (Rose and Friedman, eds., Amer. Soc. For Microbiology 1980).

Antibody fragments include any portion of the antibody which includes the paratope and is capable of binding a cytokine of interest. Antibody fragments specifically include F(ab')₂, Fab, Fab' and Fv fragments. These can be generated from any class of antibody, but typically are made from IgG or IgM. They may be made by conventional recombinant DNA techniques or, using the classical method, by proteolytic digestion with papain or pepsin. See *Current Protocols in Immunology*, chapter 2, (Coligan et a., eds., John Wiley & Sons 1991–92).

F(ab')₂ fragments are typically about 110 kDa (IgG) or about 150 kDa (IgM) and contain. two antigen-binding regions, joined at the hinge by disulfide bond(s). Virtually all, if not all, of the Fc is absent in these fragments. Fab' fragments are typically about 55 kDa (IgG) or about 75 kDa (IgM) and can be formed, for example, by reducing the disulfide bond(s) of an F(ab')₂ fragment. The resulting free sulfhydryl group(s) may be used to conveniently conjugate Fab' fragments to other molecules, such as localization signals.

Fab fragments are monovalent and usually are about 50 kDa (from any source). Fab fragments include the light (L) and heavy (H) chain, variable ($V_L$ and $V_H$, respectively) and constant ($C_L$ $C_H$, respectively) regions of the antigen-binding portion of the antibody. The H and L portions are linked by one or more intramolecular disulfide bridges.

Fv fragments are typically about 25 kDa (regardless of source) and contain the variable regions of both the light and heavy chains ($V_L$ and $V_H$, respectively). Usually, the $V_L$ and $V_H$ chains are held together only by non-covalent interactions and, thus, they readily dissociate. They do, however, have the advantage of small size and they retain the same binding properties of the larger Fab fragments. Accordingly, methods have been developed to crosslink the $V_L$ and $V_H$ chains, using, for example, glutaraldehyde (or other chemical crosslinkers), intermolecular disulfide bonds (by incorporation of cysteines) and peptide linkers. The resulting Fv is now a single chain (i.e., scFv).

Antibodies also include single chain antibodies and fragments (U.S. Pat. No. 4,946,778; Bird, Science 242:423–426 (1988); Huston et al., Proc. Natl. Acad. Sci. USA 85:5879–5883 (1988); and Ward et al., Nature 334:544–546 (1989)). Single chain antibodies are formed by linking the heavy and light chain fragments of the Fv region via an amino acid bridge, resulting in a single chain FV (scFv).

Some exemplary non-limiting kits contain at least one cytokine-specific reagent that is specific for FLT3-L, TNF-α or TGF-β. In one aspect of the invention, the reagent comprise an enzyme-linked antibody or antibody fragment.

2. Adapting the Reagent to Detect a Threshold

The kits of the invention detect a specific threshold of cytokine, which correlates with the myelosuppressive state of the patient. Such thresholds, and their determination, are detailed below. For convenience, it is advantageous to adapt the cytokine-specific detection reagent(s) to detect a certain threshold. In this way, a "yes" or "no" answer can be provided, generally indicating whether the patient is myelosuppressed or not. Thus, for example, calorimetric detection might be employed, whereby the presence of color indicates that a threshold level, correlating with the myelosuppressive state, has been reached.

Typically, the reagents of various assays (e.g., ELISAs, RIAs, and the like) will be able to detect levels of the target cytokine(s) that are lower than the threshold, i.e., they are more sensitive than they need to be. The artisan will be well-aware of methods of reducing the sensitivity of the present systems in order to provide a signal at a given threshold level. A particularly useful kit will include a reagent system that can provide a "yes" or "no" answer as to whether a patient has recovered sufficiently from myelosuppression to tolerate further cytotoxic therapy.

3. Using the Kits of the Invention

The kits may be adapted for private to commercial-scale use, for the convenience of the individual clinician, the clinical research center and even commercial diagnostic laboratories. For example, in a private clinical setting, a "dipstick"-type arrangement may be convenient. In one aspect, the cytokine-specific detection reagent may come applied to the dipstick. Thus, the kit may be used by contacting a patient sample to the dipstick-associated reagent. The detection reagent may then be visualized using conventional colorimetric means, for example. Of course, another arrangement may call for contacting the sample with the dipstick, and then application of the cytokine-specific detection reagent; the exact arrangement is a matter of choice.

In another example especially suitable for larger laboratories, the kits can be implemented in microtiter plates (e.g., 96-well plates). The same arrangement of reagents would apply, where the detection reagent is either supplied in the plate or is added after the sample is applied to the plate. In any event, given the availability of high-throughput readers for microtiter plates, very large numbers of samples could be handled automatically in this manner. Again, specific arrangements are a matter of design choice.

D. Methods of the Invention

The invention provides a general method of assessing the myelosuppressive state of a patient. The basic method comprises comparing the amount of at least one cytokine to a threshold level. The myelosuppressive state of the patient is then gauged relative to that threshold. The cytokines monitored, as explained above, may be early stimulatory or inhibitory cytokines, or combinations thereof. In one aspect, the method involves at least monitoring levels of FTL3-L.

When plasma samples are used in the present methods, it is advisable to assure the amounts measured are a function of marrow cell production, and not peripheral blood cell or tumor cell production. Fortunately, peripheral blood cells by themselves are unable to produce most cytokines. In fact, PCR amplification of reverse-transcribed RNA from peripheral blood cells in healthy individuals reveals that TGFβ, MIP-1α and IL-1β were expressed, but that SCF, IL-6, G-CSF, GM-CSF, IL-1α were not expressed. Cluitmans et a., Ann. Hematol. 75(1–2):27–31 (1997). Moreover, tumor-produced cytokines may confound marrow-produced cytokines. Several cytokines including TGFβ and TNFα are elevated in blood samples from ovarian, cervical, and endometrial cancer patients. Chopra et al., J. Cancer Res. Clin. Oncol. 123:167–172 (1997); Chopra et al., Cancer J. Sci. Am. 2:279–285 (1996); Chopra et al., Cancer Investigation 16(3):152–159 (1998). However, there is no indication whether this is true for all cancer types or that there is any evidence that FLT3-L, SCF, or MIP-1α are produced by tumors. The artisan will readily understand how to test and control for marrow-derived production.

The inventive methods may be used in conjunction with conventional therapies that induce myelosuppression. Thus, where the threshold level is approached or crossed, therapy generally will be halted or reduced. If a patient is then re-tested, and this test indicates that the threshold is no longer approached or crossed, therapy may resume. On the other hand, where a patient is being treated, and the inventive test indicates that the threshold has not been approached or crossed, the next therapeutic dose may be administered safely. In this manner, dosing regimens may be informed by constant monitoring, increasing dose and frequency until threshold levels are approached or crossed, at which point dosing may be decreased or eliminated. In this context, a threshold level is "approached" when a cytokine level is within at least about 15% of the threshold number, but preferably is within at least about 10% of the threshold.

Preferred cytokines for monitoring in the present methods include FLT3-L, TNF-α and TGF-β. Since FLT3-L is an early stimulatory cytokine, the relevant threshold is a maximum. On the other hand, since TNF-α and TGF-β are inhibitory cytokines, the relevant threshold is a minimum. Exemplary threshold levels include: at least about 135 pg/ml of plasma for FTL3-L; at most about 0.5 pg/ml of plasma for TNF-α; and at most about 15 pg/ml of plasma for TGF-β. Again, it is not only these absolute thresholds that are important; the artisan will also recognize that trends toward these thresholds are significant in prediction, especially when viewed over a multi-day (1–3) temporal window.

One aspect of the invention contemplates a method of treating cancer that involves administering to a patient in need of treatment, an effective amount of an anti-cancer agent and using the present myelorecovery monitoring techniques to inform treatment, especially dosing. Thus, cytokine levels may be evaluated at intervals throughout treatment, beginning before or after the first administration of an anti-cancer agent.

Conventional anti-cancer agents include chemotherapeutics and radiation-based therapies. Chemotherapeutic agents include alkylating agents, antimetabolites, various natural products (e.g., vinca alkaloids, epipodophyllotoxins, antibiotics, and amino acid-depleting enzymes), hormones and hormone antagonists. Specific classes of agents include nitrogen mustards, alkyl sulfonates, nitrosoureas, triazenes, folic acid analogues, pyrimidine analogues, purine analogs, platinum complexes, adrenocortical suppressants, adrenocorticosteroids, progestins, estrogens, antiestrogens and androgens. Some exemplary compounds include cyclophosphamide, chlorambucil, methotrexate, fluorouracil, cytarabine, thioguanine, vinblastine, vincristine, doxorubincin, daunorubicin, mitomycin, cisplatin, hydroxyurea, prednisone, hydroxyprogesterone caproate, medroxyprogesterone, megestrol acetate, diethyl stilbestrol, ethinyl estradiol, tomoxifen, testosterone propionate and fluoxymesterone. The known dosing protocols for these drugs may be optimized using the present methods of evaluating myelosuppression.

EXAMPLES

Example 1

This example provides methods useful for practicing the invention.

Patient Population and Collection of Patient Blood. Solid tumor patients enrolled in Institutional Review Board-approved Garden State Cancer Center clinical radioimmunotherapy ("RAIT") trials have had multiple cycles of previous chemotherapy using various drugs (e.g., doxorubicin, methotrexate, topotecan, cyclohexylchloroethylnitrosourea (CCNU), mitomycin, etc.) and different durations ranging from 1 to 24 months since their previous treatment. Juweid et al., Cancer 80:2749–2753 (1997). Patient blood (3 ml) was collected on the day of scheduled radioimmunotherapy into citrate-tubes and complete blood counts (CBCs) were performed to establish pWBC and PLT counts. Blood was collected every 3–7 days after RAIT and the maximum percent loss, and toxicity grade for both WBCs and PLTs were determined.

Plasma Cytokine Immunoassays. Plasma FLT3-L, SCF, and TGF-β in patient blood samples were measured by R&D Quantikine Immunoassay kits (Minneapolis, MN). These assays employ a quantitative sandwich enzyme immunoassay. The optical density (OD) at 570 nm is subtracted from the OD at 450 nm to correct for plate imperfections. Average duplicate readings for each sample are read from a linear standard curve. TNFα and MIP-1α were analyzed by CYTImmune Sciences' competitive enzyme immunoassay kits (College Park, Md.), resulting in an inverse relationship between OD and concentration. The kits use an amplified color generation system in which the alkaline phosphatase reaction provides a cofactor that initiates a redo cycling reaction leading to the formation of a colored (formazan) red product. The OD was read at 492 nm. All assay kits have high sensitivity, are specific, and show no significant cross-reactivity with any other murine or human cytokine.

Red Marrow Dosimetry. The red marrow dose was estimated in all patients from the cumulated activity in the blood based on the blood clearance data, and taking into account the contribution from the whole body activity. The use of a marrow/blood activity concentration ratio of 0.36 was used, which is consistent with the recommendations of the Dosimetry Task Group of the American Association of Physicists in Medicine. Siegel et al., Antibody Immunoconj. Radiopharm. 3:213–233 (1990); Fisher eta!., Cancer 73:905–911 (1994); Sgouros et al., J. Nucl. Med. 34:689–694 (1993). The corrected blood activity concentration was always multiplied by 1,500, the weight in grams of the marrow in an average adult. The mean dose in cGy was then obtained according to the MIRD schema, taking into account the contribution from the whole body activity. Loevinger et al., Soc. Nucl. Med. (1976); Cloutier et a/., J. Nucl. Med. 14:53–55 (1973).

Toxicity Assessment Myelotoxicity was graded according to the National Cancer Institute (NCI) toxicity criteria. All patients given therapeutic doses were followed for hematological toxicity by monitoring CBCs weekly. In case a grade 2 thrombocytopenia or leukopenia developed, biweekly measurements were taken, and in the case of grade 3 or 4 thrombocytopenia or leukopenia, measurements were taken every other day until the nadir had been determined. The patient's blood counts were followed until complete hematological recovery was established.

Statistical Analysis. Single factor analysis of variance (F-test) was performed on serum cytokine measurements in normal volunteers, chemotherapy naive cancer patients, and cancer patients with either normal levels, lower-than-expected levels, or higher-than-expected levels of myelosuppression for their given RM dose. The ability of a single marker or a combination of serum cytokine markers to predict myelosuppressive responses was determined using the following formula: Sensitivity=[TP/(TP+FN)]; specificity=[TN/(TN+FP)]; and accuracy=[(TP+TN)/(TP+TN+FN+FP)], where TP=true positive; TN=true negative; FP=false positive; and FN=false negative.

In a true-positive, a stimulatory cytokine is elevated and/or an inhibitory cytokine is below normal and the patient experiences high-toxicity. A true-negative means the stimulatory cytokines and/or the inhibitory cytokines are normal and toxicity is within normal limits. A false-positive means a stimulatory cytokine is elevated and/or an inhibitory cytokine level is below normal, but the magnitude of toxicity is within the. expected range or low. A false-negative means stimulatory and/or inhibitory cytokines are within normal limits, but toxicity is high and could not be predicted. An alternative clinically useful measure to express test efficiency is the likelihood ratio to characterize behavior of the diagnostic test. The positive likelihood ratio (LR+) is defined as the ratio of sensitivity over (1-specificity). When it exceeds 1, the odds favoring positive diagnosis increase, and as it approaches 1, the test is indeterminate. The negative likelihood ratio (LR-) is defined as (1-sensitivity) over specificity. Simel et al., J. Clin. Epidemiol. 44:763–770 (1991).

Example 2

This example demonstrates how to ascertain a statistically significant threshold level of a given cytokine. The methodology is set out in Example 1.

Seventy-four solid-tumor patients were selected from an initial ninety-nine patients by omitting all individuals with bone marrow metastases and all patients with an initial WBC or PLT count that was unusually high (>10,000 WBC/mm$^3$ or >550,000 PLT/mm$^3$). All patients were refractory to chemotherapy and entered clinical RAIT trials at our research center. The RM dose delivered from the therapeutic dose was calculated for each person. WBC and PLT toxicity were determined at the nadir as the percent loss from the initial count (upper panels) or as grade toxicity (lower panels), and the results plotted against the RM dose (FIG. 1). The majority of patients (52–56 out of 74 for percent loss and 40–44 out of 74 for grade toxicity) conformed to a well-defined linear relationship between RM dose and toxicity (○).

However, some patients (8 to 13) clearly exhibited less toxicity than was expected, given their RM dose (Δ) and other patients experienced much greater toxicity (9 to 15) than most other patients did (●). Using percent loss, only 5 individuals who did not fit the linear pattern deviated for both WBCs and PLTs, 2 with excess toxicity for both and 3 with less-than-expected toxicity for both. Thirteen had excess PLT toxicity with normal WBC toxicity and 5 had excess WBC toxicity and normal PLT toxicity. Using grade of toxicity as a criterion, 7 individuals deviated from expectations; 2 with excess WBC and PLT toxicity and 5 with less toxicity for both than was expected. An additional 8 patients had excess PLT toxicity with normal WBC toxicity and 7 had excess WBC toxicity, but normal PLT toxicity (Table 1A).

Since an excess toxicity of either WBC or PLT becomes dose-limiting, all patients who deviated even in one category would benefit from availability of a marker to predict excess toxicity. Of those individuals with excess PLT toxicity (15 with excess % loss and 10 with excess grade), 9 were elevated for both, only 1 had excess grade but a normal % loss and 5 had an excess % loss, but a normal grade toxicity. Of those individuals with excess WBC toxicity (9 with excess % loss and 11 with excess grade toxicity), 5 were high for both parameters measured, and 6 were high for grade toxicity but had a normal % loss, and 3 had a high % loss but a normal grade toxicity (Table 1B). If patients demonstrate a high initial WBC and/or PLT count on the day of RAIT (upper end of normal range), they could conceivably experience a high percent loss but a reasonable grade toxicity. If WBC and/or PLT counts start out at the low end of the normal range on the day of RAIT, then the patient may experience a high grade toxicity but not a high percent loss.

TABLE 1

Summary of the Number of Patients with Abnormal Degree of Toxicity in Response to RAIT (based on scattergram in FIG. 1)

A. Effect on WBCs and/or PLTs

| Measurement: | Both WBCs and PLTs Effected | | WBCs only Effected | | PLTs only Effected | |
|---|---|---|---|---|---|---|
| | High | Low | High | Low | High | Low |
| Percent Loss | 2 | 3 | 5 | 6 | 13 | 5 |
| Grade Toxicity | 2 | 5 | 9 | 6 | 8 | 8 |

Note: Total of 74 patients included in the analysis.

B. Percent Loss and Grade Toxicity

| | N | Excess % Loss | Excess Grade | Excess-Both | Excess Grade-Normal % Loss | Excess % Loss - Normal Grade |
|---|---|---|---|---|---|---|
| Excess PLT Toxicity | 16 | 15 | 10 | 9 | 1 | 6 |
| Excess WBC Toxicity | 15 | 11 | 9 | 5 | 6 | 4 |

Note: All patients has multiple cycles of chemotherapy between 1 and 24 mo. prior to entering these RAIT clinical trials.

From the patients described, thirty-nine individuals were selected and sorted them into three subgroups, the first showing "normal" WBC and PLT toxicity (N=14), the second showing low toxicity (N=13), and the third demonstrating "high" WBC or PLT toxicity (N=12). As shown in Table 2, the three groups received similar RM doses (139±28 vs. 190±32 vs. 141±51 cGy, respectively). All three groups had similar initial WBC (6,000±2,000/mm$^3$ in the first group vs. 8,000±2,000/mm$^3$ in the latter two groups) and initial PLT counts (280,000±112,000/mm$^3$ vs. 233,000±84,000/mm$^3$ vs. 203,000±65,000/mm$^3$, respectively). The group referred to as excess toxicity had a significantly higher PLT loss (81±11% vs. 54±20% in the normal toxicity group; p<0.001) and Grade PLT toxicity (3±1 vs. 1±1; p<0.001). The group also had a higher grade WBC toxicity (2±1 vs. 1±1; p<0.05).

TABLE 2

Patient Group Characteristics for Cytokine Marker Studies.

| Variable | Normal Toxicity (N = 14) | Low Toxicity (N = 13) | Excess Toxicity (N = 12) |
|---|---|---|---|
| Months Post Chemotherapy | 4 ± 6 (range: 2 to 18) | 7 ± 9 (range: 2 to 24) | 5 ± 4 (range: 1 to 13) |
| RM Dose (cGy) | 139 ± 28 | 190 ± 32 | 141 ± 51 |
| Initial pWBC Count/μl (× 1000) | 6 ± 2 | 8 ± 2 | 8 ± 2 |
| Initial PLT Count/μl (× 1000) | 260 ± 112 | 233 ± 84 | 203 ± 65 |
| % pWBC Loss Post RAIT | 45 ± 21 | 42 ± 18 | 52 ± 25 (p < 0.1 = NS)* |
| % PLT Loss Post RAIT | 54 ± 20 | 43 ± 14 (p < 0.06) | 81 ± 11 (p < 0.001) |
| Grade pWBC Toxicity Post RAIT | 1 ± 1 | 0 ± 1 (p < 0.06) | 2 ± 1 (p < 0.05) |
| Grade PLT Toxicity Post RAIT | 1 ± 1 | 0 ± 0 (p < 0.01) | 3 ± 1 (p < 0.001) |

*p values are relative to normal toxicity group

Figure 2:
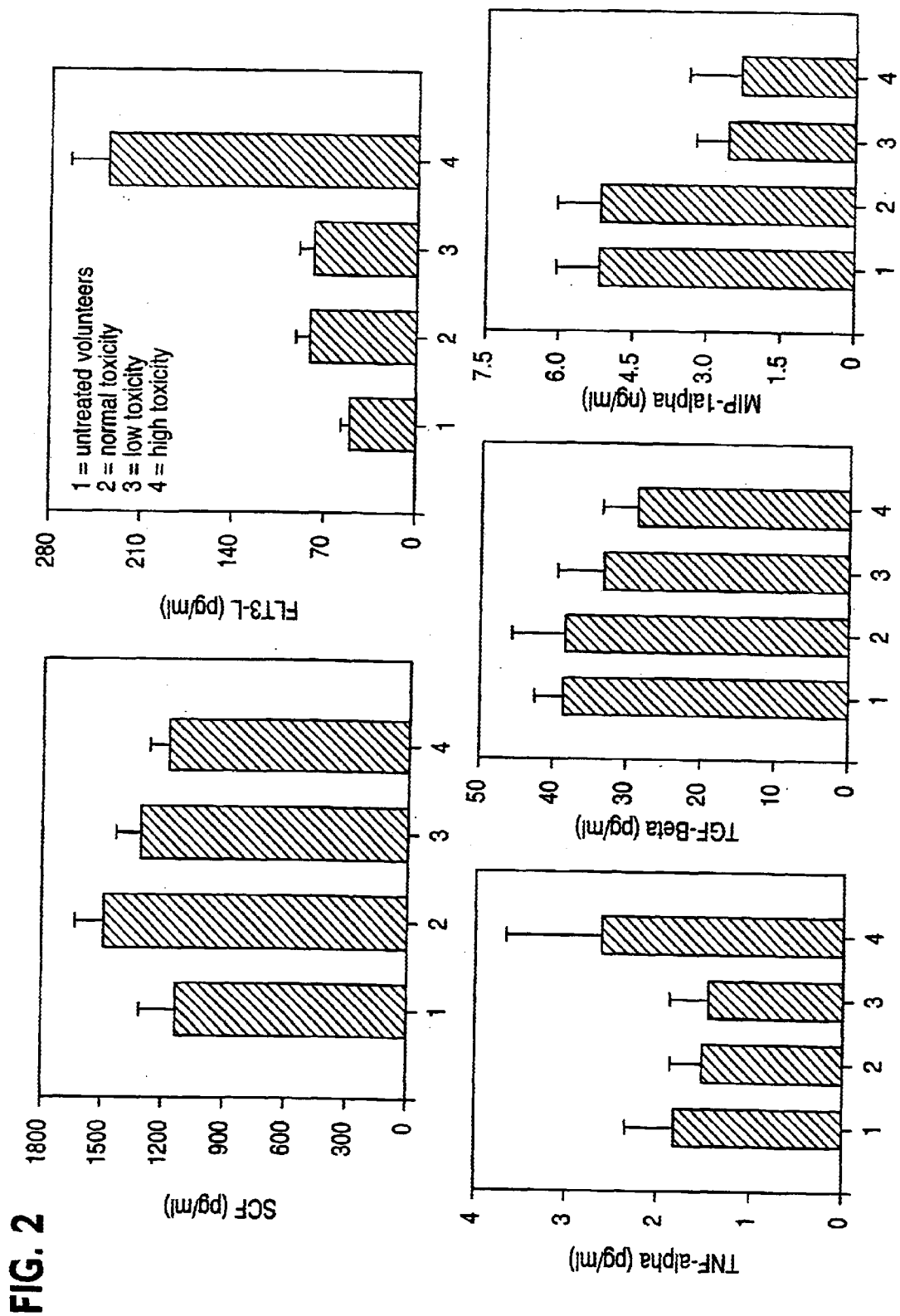
FIG. 2. Plasma cytokine levels for SCF, FLT3-L, TNFα, TGFβ and MIP-1α (mean±SEM) for 5 untreated volunteers, for 14 patients derived from the normal degree of toxicity group (open circles from FIG. 1), for 13 patients with lower than expected toxicity (triangles in FIG. 1) and 12 patients with higher than expected toxicity (solid squares in FIG. 1).

Five cytokines in patient plasma (FIG. 2) were tested for statistical correlation to myelorecovery. Table 3 shows the cytokines tested and the characteristics of the assays used.

TABLE 3

Characteristics of Cytokine Immunoassays

|  | FLT3-L | SCF | TGFβ1 | TNFα | MIP-1α |
|---|---|---|---|---|---|
| Sensitivity | 7 pg/ml | 9 pg/ml | 7 pg/ml | 0.2 ng/ml | 0.2 ng/ml |
| Linearity (range %) | 105% | 104% | 103% | — | — |
| Range | 0 to 1000 pg/ml | 0 to 2000 pg/ml | 0 to 2000 pg/ml | 0.2 to 50 ng/ml | 0.2 to 50 |
| Recovery | 94–110% | 84–112% | 94–110% | — | 85–104% |
| Normal values | 58.6 to 130.9 | 1000 to 1790 | 15.6 to 32.4 | 1.0 to 5.0 | 15 to 46 |
| Cross-reactivity | — | — | TGF-β5-1.5% TGF-β3-0.9% | — | — |

SCF was similar in all groups studied; 1498±136 pg/ml vs. 1311±119 pg/ml vs. 1177±102 pg/ml for the normal, low, and high toxicity groups compared with 1138±183 pg/ml in untreated volunteers and 1060±217 pg/ml for cancer patients who received no prior chemotherapy. In contrast to results with SCF, the other stimulatory cytokine, FLT3-L, showed a significant elevation in the excess-toxicity group (235±29 pg/ml; p<0.001) compared with patients with normal or low toxicity (81±11 pg/ml and 79±12 pg/ml, respectively), or with untreated volunteers (52±6 pg/ml).

Surprisingly, while a reduction in inhibitory cytokines was postulated to exist in the excess toxicity group, it was found instead that plasma TNFα was higher in the excess toxicity group. This was not significantly different, however, from other groups because of a marked variability between patients (2.62±1.03 compared with normal toxicity patients 1.50±0.33 pg/ml or 1.80±0.54 pg/ml in the untreated volunteers). Plasma TGFβ was also not significantly different (28.1±4.9 pg/ml in the excess toxicity group and 38.1±7.5 in the normal toxicity group). Plasma MIP1α was significantly lower in the excess toxicity group (2.23±1.09 pg/ml vs. 5.08±0.91 pg/ml in the normal toxicity group and 5.10±1.80 in the untreated volunteers group; p<0.05). However, the low toxicity group also had reduced plasma MIP1α (2.47±0.68 pg/ml; p<0.05).

Of the five plasma cytokines evaluated, FLT3-L was found to be most informative regarding anticipated toxicity as a function of RM dose. Moreover, If patient data are sorted according to toxicity grade (<grade 3, or ≧grade 3) independent of RM dose, instead of sorting patient data by normal-, low-, or high-toxicity, the importance of FLT3-L becomes even stronger (FIG. 3). Of thirty-nine patients, 27 had<grade 3 PLT toxicity and 12 had≧grade 3 PLT toxicity (the numbers are 28 and 11 patients for WBC toxicity, respectively). The RM doses for these groups were similar. Plasma FLT3-L (mean±SEM) for PLT toxicity<grade 3 was 84.4±8.8 pg/ml and 220.6±35.7 pg/ml for PLT toxicity≧grade 3 (p<0.001). A similar tendency existed for WBC toxicity, but was not statistically significant.

The usefulness of FLT3-L alone or in combination with other plasma cytokine measurements to predict high-toxicity is presented in Table 4. Stimulatory cytokine levels were set above the upper normal limit and inhibitory cytokine levels were set below the lower normal limit, both specified in Table 3. Results are expressed as sensitivity, specificity, and accuracy; the latter measurement permits identification of both the true positives and true negatives from the total population. Of all 7 permutations evaluated, high FLT3-L levels alone (>135 pg/ml) resulted in the best values for sensitivity=0.83 (one-sided 95% confidence interval is 0.66–1). Likewise, the accuracy is 0.85 and the specificity is estimated at 0.89 (95% confidence interval being 0.79-1). Combining elevated FLT3-L levels with low TNFα or low MIP1α resulted in maximum specificity, but dramatically reduced both sensitivity (0.10 or 0.56, respectively) and accuracy (0.29 and 0.25, respectively). Alternatively, adjusting the threshold for FLT-3 to 170 pg/ml results in a reduced sensitivity of 0.62, but an increased specificity of 1.0 and no significant change in accuracy (0.87) compared with a FLT3-L cutoff of 135 pg/ml. Thus, the threshold set for FLT3-L will determine whether sensitivity or specificity is higher. By using the lower FLT3-L threshold of 135 pg/ml, we can calculate the positive and negative likelihood ratios as a means of expressing predictability of FLT3-L as a diagnostic test. The estimated positive likelihood ratio is 7.5 with a 95% confidence interval 2.5–22.5. The negative likelihood ratio is 0.19, with a 95% confidence interval of 0.05–0.67.

TABLE 4

Ability of Serum Cytokines to Predict Thrombocytopenia*

|  | Sensitivity | Specificity | Accuracy |
|---|---|---|---|
| High FLT3-L (>135 pg/ml) | 83% | 89% | 85% |
| High FLT3-L or Low TNFα (<0.5 pg/ml) | 69% | 84% | 78% |
| High FLT3-L or Low TGFβ (<15 pg/ml) | 69% | 85% | 77% |
| High FLT3-L or Low TNFα or Low TGFβ | 50% | 83% | 75% |
| High FLT3-L and Low TNFα | 10% | 100% | 29% |
| High FLT3-L or Low MIP-1α (<10 pg/ml) | 63% | 81% | 34% |
| High FLT3-L and Low MIP1α | 56% | 100% | 25% |

*N = 39; 12 with high toxicity; 13 with low toxicity; 14 with normal toxicity for the given RM dose.

Hematopoiesis proceeds under the influence of early and late stimulatory and inhibitory cytokines (Cannistra et al., Semin. Hematol. 25:173–188 (1988); Whetton et al., Biochem. Biophys. Acta. 989:111–132 (1994)). The present data now show that measuring changes in production of one or more of these growth factors may predict when recovery has occurred after previous cytotoxic therapy.

In sum, these data show that plasma FLT3-L levels predicted excess platelet toxicity in 10 out of 12 patients (mean=225±106 pg/mi) and gave a false-positive in only 3 out of 27 other patients (mean of 80±41 pg/ml). Plasma FLT3-L>135 pg/ml resulted in an 83% sensitivity and an 85% and 89% specificity and accuracy, respectively, at predicting excess toxicity from additional cytotoxic therapy. The positive likelihood ratio is 7.5 (95% confidence interval of 2.5–22.5) and the negative likelihood ratio is 0.19 (95% confidence interval of 0.05–0.67).

Accordingly, elevated plasma FLT3-L in patients who received previous chemotherapy is a predictive measure of the stage of recovery of the marrow compartment. FLT3-L seems to identify the likelihood that the patient will experience≧grade 3 thrombocytopenia if additional cytotoxic therapy is administered. Knowledge of marrow activity should permit therapy that is more aggressive by establishing the earliest possible time for dosing with any cytotoxic agent having myelosuppression as the dose-limiting toxicity.

The foregoing detailed description and Examples are merely meant to be illustrative, and not limiting in any way. The artisan will immediately appreciate that there are other aspects falling within the invention that are not specifically exemplified.

What is claimed is:

1. A kit for assessing myclosuppressive state of a patient, comprising a cytokine-specific detection reagent, wherein said cytokines-specific detection reagent comprises antibodies to cytokines selected from the group consisting of fms-like tyrosine-kinase 3 ligand (FLT3-L), tumor necrosis factor-alpha (TNF-α) and transforming growth factor-beta (TGF-β), and said reagent is adapted to detect a threshold level of at least one said cytoline, said threshold correlating with said state, and instructions for assessing said myelosuppressive state of a patient, wherein said threshold level of FLT3-L is a maximum threshold level, wherein said maximum threshold level is at least about 135 pg/ml of said FLT3-L in plasma; and wherein said threshold level of TGF-β and TNF-α is a minimum threshold level, wherein said mum threshold level is at most about 0.5 pg/ml of plasma for TNF-α, and about 15 pg/ml of plasma for TGF-β.

2. A kit according to claim 1, comprising an FLT3-L-specific detection reagent.

3. A kit according to claim 2, wherein said reagents comprise an antibody or antibody fragment.

4. A kit according to claim 1, further comprising an additional detection reagent that is specific for TNF-α or TGF-β, and said reagent is adapted to detect a threshold level of TNF-α or TGF-β, said threshold correlating with said myelosuppressive state.

5. A kit according to claim 4, wherein said additional reagent comprises an antibody or an antibody fragment.

6. A method of using a kit to measure myelosuppressive state of a patient, comprising comparing the amount of at least one cytokine in a sample from the patient with a threshold level, thereby gauging the myelosuppressive state of the patient, wherein said cytokine is selected from the group consisting of FLT3-L, TNF-α, and TGF-β, and wherein said kit is a kit according to claim 1.

* * * * *

UNITED STATES PATENT AND TRADEMARK OFFICE
CERTIFICATE OF CORRECTION

PATENT NO.    : 6,649,352 B1
DATED         : November 18, 2003
INVENTOR(S)   : Rosalyn D. Blumenthal et al.

It is certified that error appears in the above-identified patent and that said Letters Patent is hereby corrected as shown below:

<u>Column 15,</u>
Line 4, delete "cytokines" and in its place insert -- cytokine --.
Line 9, delete "cytoline" and in its place insert -- cytokine --.
Line 17, delete "mum" and in its place insert -- minimum --.

Signed and Sealed this

Sixteenth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,649,352 B1  Page 1 of 1
DATED : November 18, 2003
INVENTOR(S) : Rosalyn D. Blumenthal et al.

It is certified that error appears in the above-identified patent and that said Letters Patent is hereby corrected as shown below:

Column 15,
Line 2, delete "myclosuppressive" and in its place insert -- myelosuppressive --.
Line 4, delete "cytokines" and in its place insert -- cytokine --.
Line 9, delete "cytoline" and in its place insert -- cytokine --.
Line 17, delete "mum" and in its place insert -- minimum --.

This certificate supersedes Certificate of Correction issued March 16, 2004.

Signed and Sealed this

Fourth Day of May, 2004

JON W. DUDAS
*Acting Director of the United States Patent and Trademark Office*